United States Patent [19]

Uhlendorf et al.

[11] Patent Number: 4,600,722
[45] Date of Patent: Jul. 15, 1986

[54] 3-AMINO-1-(4,5,6,7-TETRAHYDRO-BENZO-THIAZOLYL)-2-PYRAZOLINES AND A PROCESS FOR THE TREATMENT OF INFLAMMATORY OR ALLERGIC PROCESSES IN HUMANS

[75] Inventors: Joachim Uhlendorf, Erftstadt; Harald O. Borbe, Cologne; Sigurd Leyck; Michael J. Parnham, both of Pulheim; Helmut Wetzig, Pulheim-Sinnersdorf, all of Fed. Rep. of Germany

[73] Assignee: A. Nattermann & Cie GmbH, Cologne, Fed. Rep. of Germany

[21] Appl. No.: 705,670

[22] Filed: Feb. 26, 1985

[30] Foreign Application Priority Data

Mar. 1, 1984 [DE] Fed. Rep. of Germany ....... 3407506

[51] Int. Cl.⁴ .................. A61K 31/425; C07D 417/04
[52] U.S. Cl. ..................................... 514/367; 548/162
[58] Field of Search ......................... 548/162; 514/367

[56] References Cited

U.S. PATENT DOCUMENTS 4,149,005 4/1979 Battisti et al. ................... 548/362
4,376,122 3/1983 Dusza et al. ..................... 514/367

FOREIGN PATENT DOCUMENTS 39809 11/1981 European Pat. Off. ............ 514/367
3034773 3/1978 Japan ................................. 514/367

OTHER PUBLICATIONS

Annual Drug Data Report (1981)—BW-755C.

Primary Examiner—Donald G. Daus
Assistant Examiner—Mary E. Ceperley
Attorney, Agent, or Firm—Pearne, Gordon, Sessions, McCoy, Granger & Tilberry

[57] ABSTRACT

The invention relates to new 3-amino-1-(4,5,6,7-tetrahydro-benzothiazolyl)-2-pyrazolines of the Formula I

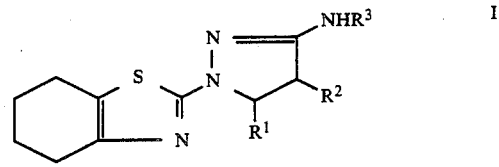

and acid addition salts thereof and a process for the treatment of inflammatory and allergic processes in humans.

5 Claims, No Drawings

3-AMINO-1-(4,5,6,7-TETRAHYDRO-BENZO-THIAZOLYL)-2-PYRAZOLINES AND A PROCESS FOR THE TREATMENT OF INFLAMMATORY OR ALLERGIC PROCESSES IN HUMANS

The invention relates to 3-amino-1-(4,5,6,7-tetrahydrobenzothiazolyl)-2-pyrazolines and physiologically acceptable acid addition salts thereof and to a process for the prophylactic or therapeutical treatment of inflammatory or allergic processes in humans.

The antiinflammatory action of 3-amino-1-(m-trifluoromethylphenyl)-2-pyrazoline (U.S. Pat. No. 4,149,005) is known (German Offenlegungsschrift No. 2,727,706).

It has now been found that 3-amino-1-(4,5,6,7-tetrahydrobenzothiazolyl)-2-pyrazolines of the formula I

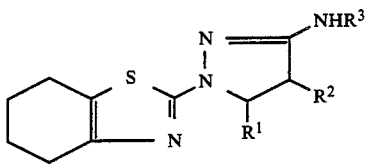

wherein $R^1$ denotes hydrogen, methyl or phenyl, $R^2$ denotes hydrogen or methyl and $R^3$ denotes hydrogen, $C_{1-4}$-alkyl or —CO—$R^4$, where $R^4$ is hydrogen, methyl, trifluoromethyl, ethyl or propyl, and pharmaceutically acceptable acid addition salts thereof, have useful pharmacological properties.

Preferred compounds of the formula I are those in which $R^1$ and $R^2$ denote hydrogen, whilst $R^3$ represents acetyl, trifluoroacetyl, ethyl or 2,2,2-trifluoroethyl. Particularly preferred compounds are those in which $R^1$, $R^2$ and $R^3$ denote hydrogen.

The invention also relates to the pharmaceutically useful acid addition salts of compounds of the formula I.

These are formed, for example, with strong inorganic acids, such as mineral acids, for example sulphuric acid, phosphoric acid or hydrogen halide acids, for example hydrochloric acid, with strong organic carboxylic acids, such as lower alkanecarboxylic acids, for example acetic acid, such as optionally unsaturated dicarboxylic acids, for example oxalic acid, malonic acid, maleic acid or fumaric acid, or such as hydroxycarboxylic acids, for example tartaric acid or citric acid, or with sulphonic acids, such as lower alkane- or optionally substituted benzene-sulphonic acids, for example methane- or p-toluene-sulphonic acid.

Examples of compounds according to the invention are: 3-amino-1-(4,5,6,7-tetrahydro-benzothiazolyl)-2-pyrazoline, 3-amino-5-methyl-1-(4,5,6,7-tetrahydro-benzothiazolyl)-2-pyrazoline, 3-acetylamino-1-(4,5,6,7-tetrahydro-benzothiazolyl)-2-pyrazoline, 3-ethylamino-1-(4,5,6,7-tetrahydro-benzothiazolyl)-2-pyrazoline, 3-trifluoroacetylamino-1-(4,5,6,7-tetrahydro-benzothiazolyl)-2-pyrazoline, 3-(2,2,2-trifluoroethylamino)-1-(4,5,6,7-tetrahydro-benzothiazolyl)-2-pyrazoline, 3-amino-4-methyl-1-(4,5,6,7-tetrahydro-benzothiazolyl)-2-pyrazoline, 3-amino-5-phenyl-1-(4,5,6,7-tetrahydro-benzothiazolyl)-2-pyrazoline, 5-methyl-3-propionamido-1-(4,5,6,7-tetrahydro-benzothiazolyl)-2-pyrazoline, 3-formamido-5-phenyl-1-(4,5,6,7-tetrahydro-benzothiazolyl)-2-pyrazoline, 3-butyramido-4-methyl-1-(4,5,6,7-tetrahydro-benzothiazolyl)-2-pyrazoline, 3-methylamino-5-phenyl-1-(4,5,6,7-tetrahydro-benzothiazolyl)-2-pyrazoline, 3-propylamino-5-methyl-1-(4,5,6,7-tetrahydro-benzothiazolyl)-2-pyrazoline, 3-butylamino-4-methyl-1-(4,5,6,7-tetrahydro-benzothiazolyl)-2-pyrazoline, 3-acetamido-5-phenyl-1-(4,5,6,7-tetrahydro-benzothiazolyl)-2-pyrazoline, 3-ethylamino-5-phenyl-1-(4,5,6,7-tetrahydro-benzothiazolyl)-2-pyrazoline, 3-butyramido-5-phenyl--(4,5,6,7-tetrahydro-benzothiazolyl)-2-pyrazoline and 3-butylamino-5-phenyl-1-(4,5,6,7-tetrahydro-benzothiazolyl)-2-pyrazoline.

The compounds of the formula I display useful pharmacological properties. In particular, they inhibit the lipoxygenase and cyclooxygenase breakdown pathways of arachidonic acid metabolism and hence the formation of leukotrienes and prostaglandins. They are therefore employed as medicaments for the treatment of inflammatory and allergic processes in humans and are used as antiinflammatories, antirheumatics, antiatherosclerotics, antithrombotics, antiallergics, antiasthmatics and gastroprotectives.

The compounds according to the invention where $R^3$=H are prepared by processes which are known per se, for example according to G. F. Duffin and J. D. Kendall, J. Chem. Soc. 1954, 408–415, by base-catalysed cyclocondensation of 2-hydrazino-4,5,6,7-tetrahydrobenzothiazole II

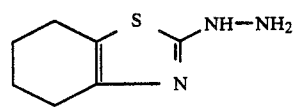

with unsaturated nitriles of the formula III

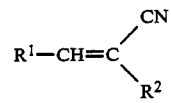

wherein $R^1$ and $R^2$ have the meanings given in formula I.

The reaction is carried out in a suitable solvent, preferably in lower alcohols, at temperatures of 50°–100° C. in the presence of an alkali metal alcoholate under a protective gas atmosphere (for example nitrogen).

The compounds I ($R^3$=$C_{1-4}$-acyl) are prepared from the compounds I ($R^3$=H) by known acylation processes with carboxylic acid halides or anhydrides in the presence or absence of a suitable solvent at 0°–60° C.

The representatives of I ($R^3$=$C_{1-4}$-alkyl) are obtained by reduction of the acyl compounds. All the processes for the reduction of carboxylic acid amides can be used for this. The use of complex metal hydrides, in particular lithium aluminium hydride, in a solvent is very advantageous. Normal and cyclic ethers, such as diethyl ether, dioxane and tetrahydrofuran, at temperatures up to the boiling point of the solvent are suitable for this.

The present invention also relates to pharmaceutical products which contain compounds of the formula I or pharmaceutically useful acid addition salts of these compounds. The pharmaceutical products according to the invention are those for enteral, such as oral or rectal, and parenteral administration, which contain the pharmaceutical active compounds by themselves or together with a customary pharmaceutically usable excipient. The pharmaceutical formulation of the active compound is advantageously in the form of individual doses adapted for the desired administration, such as, for example, tablets, coated tablets, capsules or suppositories. In the case of oral administration, the dosage of the compounds is usually between 10 and 1,000 mg per day, preferably between 30 and 300 mg, and can be administered in one or several portions, preferably two or three portions, daily.

The preparation of the compounds according to the invention is illustrated in more detail by the following examples. The melting points given were measured with a Büchi 510 melting point determination apparatus, and are given in °C. and are uncorrected.

EXAMPLE 1

3-Amino-1-(4,5,6,7-tetrahydro-benzothiazolyl)-2-pyrazoline hydrochloride 26.4 g of 2-hydrazino-4,5,6,7-tetrahydro-benzothiazole are added to a sodium methylate solution prepared from 5.5 g of sodium and 260 ml of absolute ethanol, and, after 15 minutes, 6.8 g of acrylonitrile are added, with stirring. After stirring under reflux for about 8 hours, the solvent is stripped off in vacuo, the residue is taken up in water and the mixture is extracted twice with 150 ml of chloroform each time. The chloroform phase is washed, dried and concentrated to give 19.8 g of a brown oil, which gradually crystallises completely. The crystal sludge is washed thoroughly on the frit with acetone and ether. After drying, 9.3 g of beige crystals of chromatographically pure 3-amino-1-(4,5,6,7-tetrahydro-benzothiazolyl)-2-pyrazoline of melting point 213°-215° C. are obtained.

The base is dissolved in methanol and ethereal HCl is added dropwise. The solid is filtered off and recrystallised from ethanol. 7.1 g of 3-amino-1-(4,5,6,7-tetrahydro-benzothiazolyl)-2-pyrazoline hydrochloride of melting point 270°-272° C. are obtained.

The 2-hydrazino-4,5,6,7-tetrahydro-benzothiazole hydrochloride used above is prepared in accordance with the method of Y.Usui [CA 70,96685 (1969)] via Hantzsch synthesis, with better yields by modification of the conditions. A mixture of 20 g of formylthiosemicarbazide, 22.3 g of 2-chlorocyclohexanone and 150 ml of dimethylformamide is kept at 70°-80° C. for 3 hours. On cooling, some of the product crystallises out. The dimethylformamide is distilled off in vacuo and the residue is recrystallised from ethanol. 27.4 g of 1-formyl-2-(4,5,6,7-tetrahydro-benzothiazolyl)-hydrazine hydrochloride of melting point 171°-173° C. are obtained.

A solution of 40.2 g of 1-formyl-2-(4,5,6,7-tetrahydro-benzothiazolyl)-hydrazine hydrochloride in 400 ml of ethanol and 100 ml of concentrated hydrochloric acid is boiled under reflux for 4 hours. Concentration of the mixture and drying of the residue gives 41.5 g of 2-hydrazino-4,5,6,7-tetrahydro-benzothiazole hydrochloride of melting point 177°-179° C. as a hygroscopic substance of sufficient purity for further reactions.

EXAMPLE 2

3-Amino-5-methyl-1-(4,5,6,7-tetrahydro-benzothiazolyl)-2-pyrazoline 20 g of 2-hydrazino-4,5,6,7-tetrahyro-benzothiazole hydrochloride are added to a sodium ethylate solution of 5.7 g of sodium and 250 ml of ethanol and the mixture is stirred at room temperature for 10 minutes. 5.5 g of crotononitrile are then added dropwise and the mixture is boiled under reflux for 5 hours. After cooling, the ethanol is stripped off in vacuo and the residue is taken up in water. The insoluble material is filtered off and washed thoroughly with water, acetone and ether in succession. After drying, 11.8 g of beige crystals of 3-amino-5-methyl-1-(4,5,6,7-tetrahydro-benzothiazolyl)-2-pyrazoline of melting point 247°-249° C. are obtained.

EXAMPLE 3

3-Acetylamino-1-(4,5,6,7-tetrahydro-benzothiazolyl)-2-pyrazoline hydrochloride 3 g of 3-amino-1-(4,5,6,7-tetrahydro-benzothiazolyl)-2-pyrazoline and 7.7 g of acetyl chloride are stirred at room temperature for about 17 hours, until the thin layer chromatogram no longer shows any starting material. The mixture is partitioned between chloroform and water and the solid is filtered off and triturated with ether.

1.15 g of white crystals of 3-acetylamino-1-(4,5,6,7-tetrahydro-benzothiazolyl)-2-pyrazoline hydrochloride of melting point 256°-258° C. are obtained.

EXAMPLE 4

3-Ethylamino-1-(4,5,6,7-tetrahydro-benzothiazolyl)-2-pyrazoline hydrochloride

A solution of 2 g of 3-acetylamino-1-(4,5,6,7-tetrahydro-benzothiazolyl)-2-pyrazoline in 50 ml of absolute ether is added dropwise to a suspension of 0.72 g of lithium aluminium hydride in 50 ml of absolute ether at room temperature. After 16 hours at the reflux temperature, the mixture is cooled and water is carefully added, while cooling with ice. The residue is filtered off and washed with ether. The ether phase is separated off and the aqueous phase is extracted twice with ether. The organic phase is washed, dried over sodium sulphate and concentrated. The residue is purified by column chromatography on silica gel. The main fraction eluted with chloroform/5% of methanol gives 0.9 g of base, which is recrystallised as the hydrochloride from ethanol. 0.6 g of 3-ethylamino-1-(4,5,6,7-tetrahydro-benzothiazolyl)-2-pyrazoline hydrochloride of melting point 255°-257° C. are obtained.

EXAMPLE 5

The following compounds are prepared by the method of Examples 1 to 4: 3-amino-4-methyl-1-(4,5,6,7-tetrahydro-benzothiazolyl)-2-pyrazoline, melting point 210°-212° C., 3-amino-5-phenyl-1-(4,5,6,7-tetrahydro-benzothiazolyl)-2-pyrazoline, melting point 244°-247° C., 3-trifluoroacetylamino-5-methyl-1-(4,5,6,7-tetrahydro-benzothiazolyl)-2-pyrazoline, melting point 199°-201° C.

We claim:

1. 3-Amino-1-(4,5,6,7-tetrahydro-benzothiazolyl)-2-pyrazolines of the Formula I

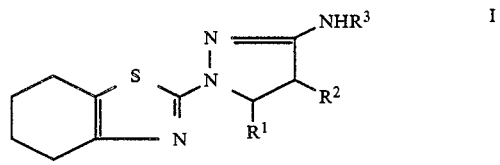

wherein $R^1$ is a member selected from the group consisting of hydrogen, methyl and phenyl, $R^2$ is a member selected from the group consisting of hydrogen and methyl and $R^3$ is a member selected from the group consisting of hydrogen, $C_{1-4}$-alkyl, 2,2,2-trifluoroethyl and —CO—$R^4$, where $R^4$ is a member selected from the group consisting of hydrogen, methyl, trifluoromethyl, ethyl and propyl; and the pharmaceutically acceptable acid addition salts thereof.

2. Compounds according to claim 1, wherein in Formula I $R^1$, $R^2$ and $R^3$ is hydrogen.

3. Compounds according to claim 1, wherein in the Formula I $R^1$ and $R^2$ are hydrogen and $R^3$ is a member selected from the group consisting of acetyl and trifluoroacetyl.

4. Compounds according to claim 1, wherein in Formula I $R^1$ and $R^2$ are hydrogen and $R^3$ is a member selected from the group consisting of ethyl and 2,2,2-trifluoroethyl.

5. Process for the prophylactic and therapeutic treatment of inflammatory or allergic processes in humans comprising administering to a human being suffering from an inflammatory or allergic process a compound according to any one of claims 1 to 4 in a dose ranging from 10 to 1,000 mg per day.

* * * * *